(12) United States Patent
Dasher et al.

(10) Patent No.: US 8,056,401 B2
(45) Date of Patent: Nov. 15, 2011

(54) IN-LINE MOISTURE-CONTENT MEASUREMENT OF CERAMIC MATERIALS IN CERAMIC ARTICLE MANUFACTURING

(75) Inventors: David Dasher, Corning, NY (US); Robert John Locker, Corning, NY (US); James Monroe Marlowe, Corning, NY (US)

(73) Assignee: Corning Incorporated, Corning, NY (US)

( * ) Notice: Subject to any disclaimer, the term of this patent is extended or adjusted under 35 U.S.C. 154(b) by 424 days.

(21) Appl. No.: 12/471,530

(22) Filed: May 26, 2009

(65) Prior Publication Data
US 2010/0300183 A1    Dec. 2, 2010

(51) Int. Cl.
*G01N 5/02*    (2006.01)
(52) U.S. Cl. .............................. 73/73; 324/634; 324/601
(58) Field of Classification Search .............. 73/73, 623, 73/588, 594; 324/601, 634; 264/506
See application file for complete search history.

(56) References Cited

U.S. PATENT DOCUMENTS

| | | | |
|---|---|---|---|
| 3,885,977 A | 5/1975 | Lachman et al. | |
| 5,258,150 A | 11/1993 | Merkel et al. | |
| 6,620,751 B1 | 9/2003 | Ogunwumi | |
| 6,942,713 B2 | 9/2005 | Ogunwumi et al. | |
| RE38,888 E | 11/2005 | Beall et al. | |
| 7,001,861 B2 | 2/2006 | Beall et al. | |
| 7,259,120 B2 | 8/2007 | Ellison et al. | |
| 2004/0029707 A1 | 2/2004 | Beall et al. | |
| 2004/0261384 A1 | 12/2004 | Merkel et al. | |
| 2011/0006461 A1* | 1/2011 | Dasher et al. ................. | 264/408 |

* cited by examiner

*Primary Examiner* — Jewel V Thompson
(74) *Attorney, Agent, or Firm* — Walter M. Douglas

(57) ABSTRACT

In-line systems for and methods of measuring the moisture content of ceramic material within an extrusion system used to form ceramic articles are disclosed. One method includes arranging, relative to the extrusion system, at least one radio-frequency (RF) sensor system having an RF antenna, and generating through the RF antenna an RF field that resides substantially entirely within the ceramic material. The method also includes, in response to the RF field interacting with the ceramic material, generating in the RF sensor system a signal representative of a raw moisture-content measurement of the ceramic material. The method also includes generating calibration data by performing RF moisture-content measurements on samples of the ceramic material having different known moisture contents, and establishing a calibrated moisture-content measurement using the raw moisture-content signal and the calibration data. Both contact and non-contact systems and measurement methods are described.

20 Claims, 7 Drawing Sheets

IN-LINE MOISTURE-CONTENT MEASUREMENT OF CERAMIC MATERIALS IN CERAMIC ARTICLE MANUFACTURING

FIELD

The present invention relates to the manufacture of ceramic-based articles, and in particular to in-line measuring of the moisture content of ceramic material in a ceramic article manufacturing processes.

BACKGROUND

Extrusion processes are used in a variety of industries to form a wide range of products. One type of extrusion process uses a ceramic-forming material that forms a plastic mix or 'batch material" that is extruded through a die orifice to form a shaped article.

More recently, ceramic honeycomb-shaped articles having a multitude of cells or passages separated by thin walls running parallel to the longitudinal axis of the structure have been formed via extrusion and used as filters ("ceramic filters") for a variety of applications, including particulate filters for combustion engines.

A number of parameters need to be controlled in the extrusion process for the desired article to maintain its post-extrusion form and to ultimately form an article that meets is particular design and/or performance requirements. Such parameters include, for example, the particular composition of the mix that makes up the batch material, and the moisture content of extruded "logs" that can subsequently be dried (a "dried log") and fired to form a ceramic article A batch material having insufficient moisture will not extrude properly and could lead to the formation of cracks (including invisible microcracks) in the final article. On the other hand, an organic batch material having too much moisture will also not extrude properly and could lead to deformation (e.g., sagging) of the extruded article.

The moisture content of a dried log needs to be measured to determine whether it meets the dryness specification, which is typically on the order of 1% or so, prior to the dried log being cut and fired. A log having too much moisture will be damaged (e.g., "smeared") upon cutting, and can also damage the saw blade used to cut the log.

It is thus desirable to be able to measure the moisture content of ceramic-forming material used to make the ceramic articles such as ceramic filters. One moisture-content measurement technique is called "loss on drying" (LOD), which is a destructive, off-line technique that can take hours to complete. Other moisture-content measurement techniques that rely on pyrometers to measure log temperature tend to be inaccurate because they measure surface temperature, which is often significantly different from the bulk temperature (and thus the water content) of the ceramic material.

Consequently, what is needed are efficient, in-line methods and systems for measuring moisture content of the ceramic material during the ceramic article manufacturing process.

SUMMARY

An aspect of the invention is an in-line method of measuring a moisture content of ceramic material within an extrusion system used to form ceramic articles. The method includes arranging, relative to the extrusion system, at least one radio-frequency (RF) sensor system having an RF antenna, and generating through the RF antenna an RF field that resides substantially entirely within the ceramic material. The method also includes, in response to the RF field interacting with the ceramic material, generating in the RF sensor system a signal representative of a raw moisture-content measurement of the ceramic material. The method further includes generating calibration data by performing RF moisture-content measurements on samples of the ceramic material having different known moisture contents. The method also includes establishing a calibrated moisture-content measurement using the raw moisture-content signal and the calibration data.

Another aspect of the invention is an in-line method of measuring a moisture content of a substantially dry log formed from ceramic material and having a surface with a shape, and used to form a ceramic article. The method includes generating at least one RF field using at least one RF sensor arranged relative to the log so that the at least one RF field resides substantially entirely within the log. In response to the at least one RF field interacting with the ceramic material in the log, the method further includes measuring with the at least one RF sensor a corresponding at least one response signal representative of a raw moisture-content measurement in the log. The method also includes generating calibration data by performing RF moisture-content measurements on log samples made of the same ceramic material but having different known moisture contents. The method further includes using the calibration data and the at least one response signal to form at least one calibrated moisture-content measurement for the log.

Another aspect of the invention is an in-line system for measuring within an extrusion system a moisture content of ceramic material with a surface and used to form ceramic articles. The system includes at least one RF sensor system having an RF antenna and arranged relative to the extrusion system. The least one RF sensor is configured to generate an RF field through the RF antenna and substantially entirely within the ceramic material so as to generate a response signal that contains raw moisture-content information. The system also includes a computer-readable medium connected to or included within the at least one RF sensor and configured to store the raw moisture-content calibration information and to store calibration data obtained by performing RF moisture-content measurements on samples of the ceramic material having different known moisture contents. The system further includes a processor operably coupled to the computer readable medium and configured to execute instructions that cause the processor to calculate a calibrated moisture-content measurement based on the response signal and the calibration data stored in the computer-readable medium.

These and other advantages of the invention will be further understood and appreciated by those skilled in the art by reference to the following written specification, claims and appended drawings.

DETAILED DESCRIPTION

Reference is now made in detail to the present preferred embodiments of the invention, examples of which are illustrated in the accompanying drawings. Whenever possible, the same reference numbers and symbols are used throughout the drawings to refer to the same or like parts.

The systems and methods described herein are concerned with the extrusion of a plastic ceramic-based batch material into articles of widely differing profiles and shapes. The systems and methods described herein are especially concerned with the extrusion of thin-walled honeycomb structures from "ceramic-forming" batch materials capable of flowing or plastically deforming under pressure during extrusion, but which have the ability to maintain their as-extruded form under ambient conditions after being relieved of the high extrusion shear forces. More specifically, the systems and methods described herein relate to apparatus and methods for measuring, in-line and in real time, the moisture content of dried logs, newly extruded logs, or the batch material used to form the extruded logs. The in-line, real-time moisture-content measurement allows a system operator to adjust the extrusion system parameters, including for example, batch material water content and greenware drying conditions.

In the discussion below, the moisture-content measurement is of a "ceramic material," which takes on different forms in the ceramic article manufacturing process. Thus, the term "ceramic material" is a general term used to denote either dried logs, newly extruded logs, the ceramic-forming batch material used to form the extruded logs, or whatever particular form the ceramic material is in at the time the in-line moisture-content measurement is made as the ceramic material makes its way through the extrusion and forming process including pre-extruded batch material, and prior to and during the drying process (e.g., in between drying steps of a multi-step drying process). The invention described herein applies generally to ceramic articles, and is described in connection with ceramic filters and a ceramic-filter manufacturing process by way of illustration.

Figure 1:
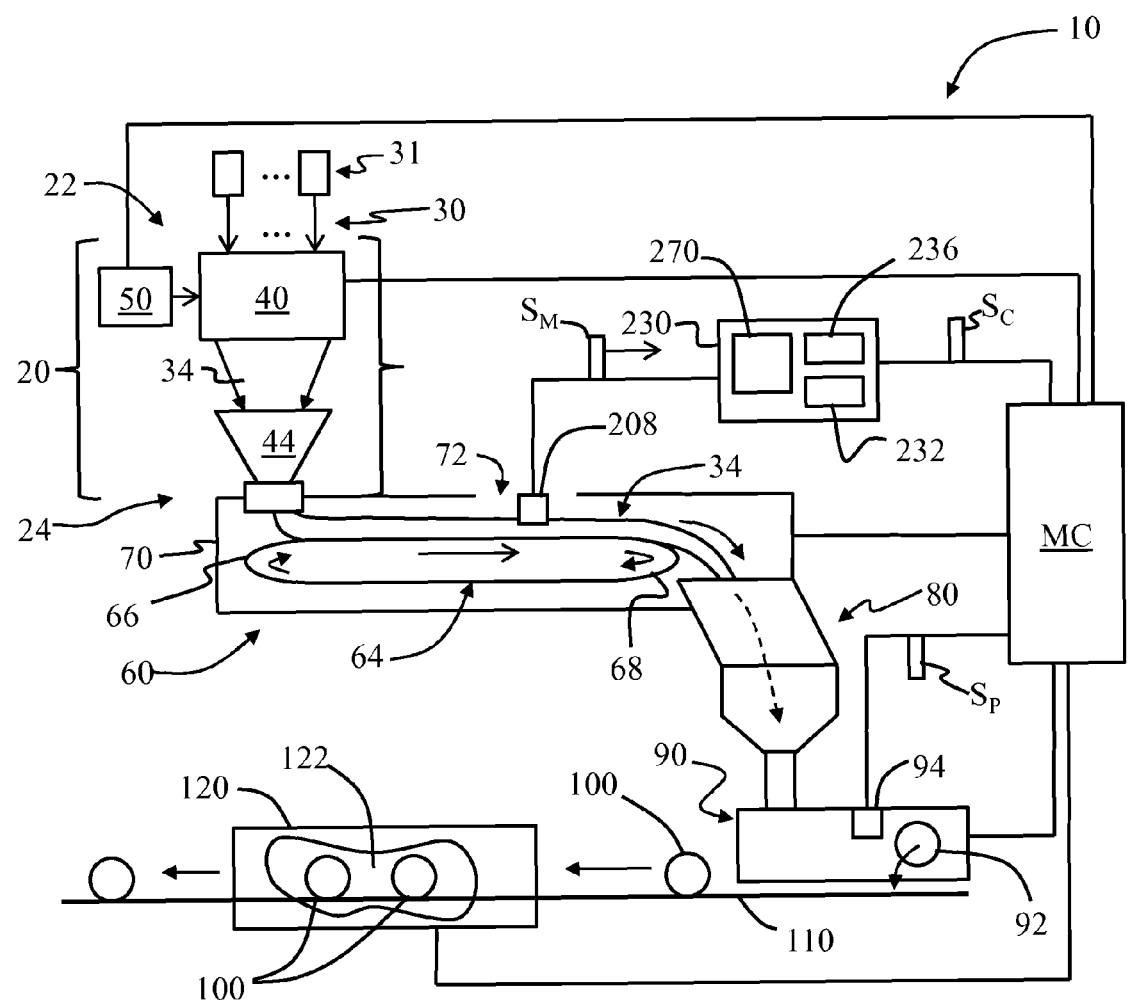
FIG. 1 is a schematic diagram of an example embodiment of an extrusion system used to form ceramic articles in the form of ceramic filters using a ceramic-forming extrusion material, and that includes an RF sensor system for measuring the moisture content of the "batch material" ceramic material.

FIG. 1 is a schematic diagram of an example embodiment of an extrusion system 10 used to form ceramic articles in the form of ceramic filters using a ceramic-forming extrusion material. Extrusion system 10 includes a mixing stage or "wet tower" 20 having an input end 22 and an output end 24. Wet tower 20 initially receives at input end 22 the various batch material constituents 30 in dry form from respective constituent sources 31, and mixes them along with water (and optionally oil) to form an initial ceramic-forming batch material 34. Wet tower 20 includes, for example, a mixer 40 followed by a rotary cone 44. Wet tower 20 also includes a water unit 50 configured to provide water to mixer 40 in select amounts, e.g., by weighing the amount of water added to the mixer. In an example embodiment, water unit 50 is controlled manually and/or automatically, as discussed below. Examples of batch material 34 are discussed below.

Extrusion system 10 further includes a conveyer unit 60 arranged adjacent output end 24 of wet tower 20. Conveyor unit 60 includes a conveyor belt 64 with an input end 66 and an output end 68. Conveyor belt 64 rotates clockwise as shown. Conveyor unit 60 includes a protective cover 70 that has, near conveyor belt output end 68, an aperture 72, the purpose of which is discussed in greater detail below. In an example embodiment, conveyor belt 64 is between 4 and 5 feet long.

Conveyor belt input end 66 is arranged at the output end 24 of wet tower 20 so as to receive batch material 34 therefrom. In an example embodiment, rotary cone 44 serves to deliver batch material 34 to conveyor belt input end 66 in a relatively uniform layer. In an example embodiment, batch material 34 is carried by conveyor belt 64 in a layer having a thickness between about one inch and about two inches and a width between about ten inches and about fourteen inches. Wet tower 20 is configured to adjust the thickness of the layer of batch material 34 carried by conveyor belt 64.

Extrusion system 10 further includes a chute 80 and an extrusion unit 90. Chute 80 is arranged between conveyor unit 60 and extrusion unit 90. Chute 80 is configured to receive batch material 34 from the output end 68 of conveyor belt 64 and deliver it to extrusion unit 90. Extrusion unit 90 is configured to receive batch material 34 and form billets therefrom, which are then pressed through an extrusion die 92 (e.g., by a twin-screw extruder) to form extrudate 100. In an example embodiment, extrusion unit 90 includes multiple extrusion dies that operate at once to simultaneously form multiple extrudates 100.

In an example embodiment, extrusion system 10 includes a pressure sensor 94 in extrusion unit 90 electrically connected to a master controller MC and configured to measure the pressure during extrusion. Pressure sensor generates an electrical signal $S_P$ that is sent to and received by master controller MC, which processes and preferably displays the pressure measurements on a display (not shown).

Extrusion system 10 also includes an RF sensor system 200, which is described in greater detail below.

Figure 2:
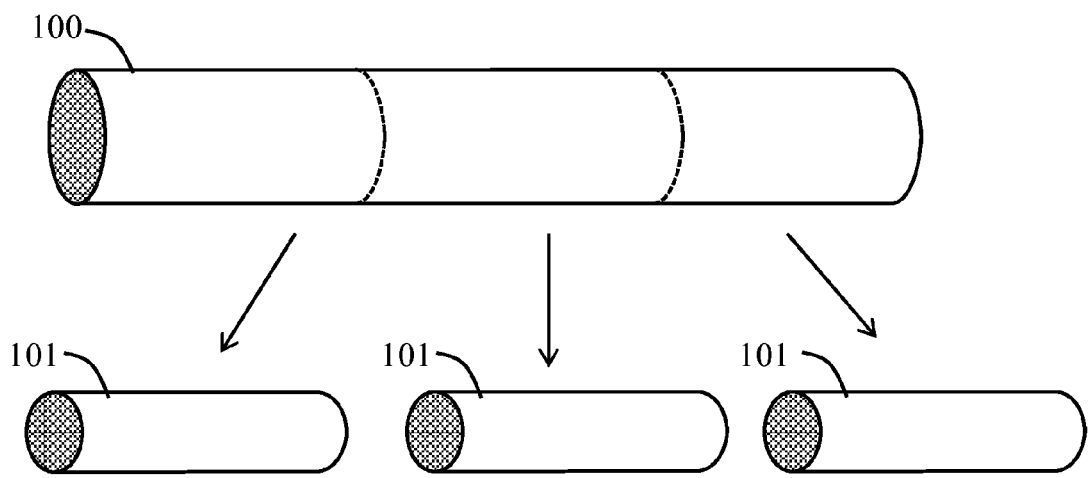
FIG. 2 is a perspective view of an example cylindrical extrudate formed by extrusion using the extrusion system of FIG. 1, and also showing how the extrudate is cut into logs.

Extrudate 100 is deposited onto a conveyor 110 arranged adjacent extrusion die 92. In an example embodiment, extrudate 100 is cut into sections called "greenwares" or "logs" 101, as shown in FIG. 2. Logs 101 may be, for example about 3 feet in length. Greenwares 101 are then conveyed by conveyor 110 to a drying station (e.g., an oven or "applicator") 120. Drying station 120 has an interior 122 where logs 101 reside while drying. Drying station 110 may use, for example, radio-frequency (RF) radiation or microwave frequency (MF) radiation, to effectuate drying.

In an example embodiment, extrusion system 10, master controller MC is also operably connected to wet tower 20 (an in particular to water unit 50 therein), to conveyor units 70 and 110, to extruder 90, to drying station 120 and to RF sensor system 200, and is configured to control the operation of these system components so as to control the overall operation of the extruder system.

The drying process is carried out until logs 101 are substantially dry, meaning that most or all of the liquid initially present in extrudate 100 has been removed so that the moisture content has been reduced to a level acceptable for cutting and firing the piece at high temperature to form the ceramic filter. In example embodiments, logs 101 contain less than 2 wt % water, or in some cases less than 1 wt % water, upon exiting drying station 110. Having the proper moisture content at this stage is critical because logs that are too moist become damaged upon cutting (e.g., are subject to "smearing"), and can also damage the cutting saw.

Figure 3:
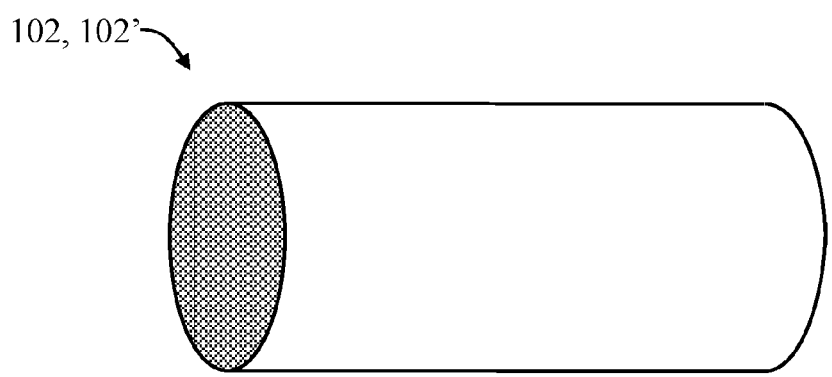
FIG. 3 is a perspective view of a greenware piece or a ceramic article in the form of a ceramic filter body, as formed by cutting up one of the logs of FIG. 2.

If logs 101 are sufficiently dry, they are cut into smaller greenware pieces 102 (see FIG. 2) and the cut pieces fired (e.g., in a hot-air oven). This transforms greenware pieces 102 into respective ceramic bodies 102' having a honeycomb structure with thin interconnecting porous walls that form parallel cell channels longitudinally extending between end faces, as shown in FIG. 3. In an example embodiment, ceramic body 102' is used to form a ceramic filter.

Exemplary ceramic bodies 102' comprised of AT-based ceramic materials are discussed in U.S. Pat. No. 7,001,861, U.S. Pat. No. 6,942,713, U.S. Pat. No. 6,620,751, and U.S. Pat. No. 7,259,120, which patents are incorporated by reference herein. Such AT-based bodies are used as an alternative to cordierite and silicon carbide (SiC) bodies for high-temperature applications, such as automotive emissions control applications. The systems and methods disclosed herein apply to any type of greenware amenable to RF or MW drying techniques.

Batch Materials

The aqueous-based ceramic precursor mixture formed in wet tower 20 preferably comprises a batch material mixture of ceramic (such as cordierite) forming inorganic precursor materials, an optional pore former such as graphite or starch, a binder, a lubricant, and a vehicle. The inorganic batch material components can be any combination of inorganic components (including one or more ceramics) which can, upon firing, provide a porous ceramic having primary sintered phase composition (such as a primary sintered phase composition of cordierite or aluminum titanate).

In an example embodiment, the inorganic batch material components can be selected from a magnesium oxide source, an alumina-forming source, and a silica source. The batch material components are further selected so as to yield a ceramic article comprising predominantly cordierite, or a mixture of cordierite, mullite and/or spinel upon firing. For example, the inorganic batch material components can be selected to provide a ceramic article that comprises at least about 90% by weight cordierite, or more preferably 93% by weight cordierite. In an example embodiment, the cordierite-containing honeycomb article consists essentially of, as characterized in an oxide weight percent basis, from about 49 to about 53 percent by weight $SiO_2$, from about 33 to about 38 percent by weight $Al_2O_3$, and from about 12 to about 16 percent by weight MgO. To this end, an exemplary inorganic cordierite precursor powder batch material composition preferably comprises about 33 to about 41 weight percent of an aluminum oxide source, about 46 to about 53 weight percent of a silica source, and about 11 to about 17 weight percent of a magnesium oxide source. Exemplary non-limiting inorganic batch material component mixtures suitable for forming cordierite are disclosed in U.S. Pat. Nos. 3,885,977; 5,258,150; US Pubs. No. 2004/0261384 and 2004/0029707; and RE 38,888, which are all incorporated by reference herein.

The inorganic ceramic batch material components can include synthetically produced materials such as oxides, hydroxides, and the like. Alternatively, they can be naturally occurring minerals such as clays, talcs, or any combination thereof, which are selected depending on the properties desired in the final ceramic body.

In one example, an "inorganic batch material" includes ceramic-based mixtures that are "substantially inorganic" because they typically include some pour-forming organics that make up a minor portion (e.g., about 1% to about 7%) of the mixture.

RF-Based Moisture-Content Measurements

The RF-based moisture-content measurements made using the systems and methods described herein rely on measuring the dielectric constant of the ceramic material. The dielectric constant $\in$ is a relative measure of the extent to which a dielectric material concentrates electrostatic lines of flux, and is the ratio of the amount of stored energy when an electrical potential is applied, relative to the permittivity $\in_0$ of a vacuum.

The dielectric constant $\in$ of ceramic material varies with water content. Since the dielectric constant of water (approximately $\in=80$ at 20° C.) is much higher than that of typical ceramic batch materials (approximately $\in=4$), it can be reasonably assumed that changes in the dielectric constant in a ceramic batch material are due essentially entirely to changes in water content. A product-specific calibration is performed to translate the dielectric constant measurements into an actual or "calibrated" moisture content of the batch material.

Figure 4:
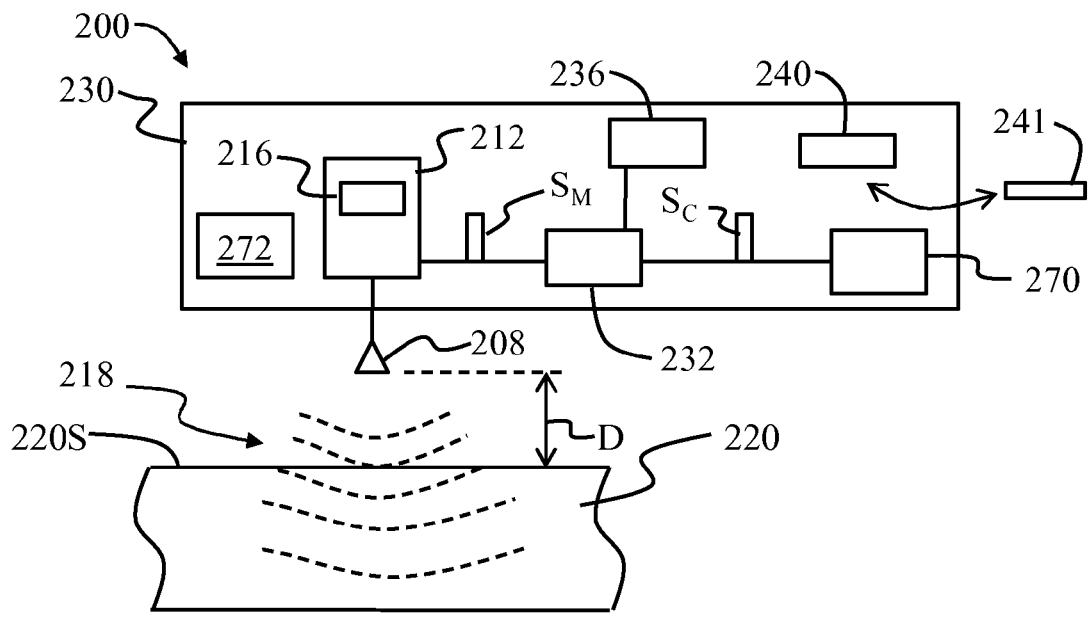
FIG. 4 is a schematic diagram of an example RF sensor system, shown relative to a section of ceramic material, that is used to measure the moisture content of the ceramic material.

The systems and methods described herein make use of an RF sensor system 200 to measure the dielectric constant of a ceramic material 220 having a surface 220S. FIG. 4 is a schematic diagram of an example RF sensor system 200 used to measure the moisture content of ceramic material 220 (a section of the ceramic material is shown). RF sensor system 200 includes an RF antenna 208 electrically connected to a parallel-tuned circuit 212, which includes a phase-lock loop 216. Antenna 208 and ceramic material 220 form a variable capacitance for parallel-tuned circuit 212. RF sensor system 200 operates by generating RF signals in parallel-tuned circuit 212 and generating an RF field 218 via RF antenna 208. RF field 218 resides substantially entirely within ceramic material 220. Thus, for example, there may be a small air gap (e.g., about 0.25 inches or about 6.35 mm) between RF antenna 208 and ceramic material surface 220S. The interaction of RF field 218 with ceramic material 220 changes the resonant frequency of parallel-tuned circuit 212. In response, parallel-tuned circuit 212 finds the new resonant frequency via the operation of phase lock loop 216. This new resonant frequency is used to determine the overall capacitance of the parallel-tuned circuit, which is then used to determine the dielectric constant of ceramic material 220. The dielectric constant is in turn used to providing a relative ("raw") measure of the moisture content of the ceramic material.

RF sensor system 200 is preferably calibrated for each particular type of ceramic material 220 and material shape (contour) to convert the relative moisture-content measurement into a calibrated moisture-content measurement. An example RF sensor system 200 is the RFM-1000 available from Process Sensors, Corp., Milford, Mass., which system operates at 3-7 MHz and uses about 12 mW of power.

The penetration depth of RF field 218 into ceramic material 220 depends in large part on the dielectric constant of the ceramic material, which is a function of the exact composition of the ceramic material as well as the water content. For logs 101 that are substantially dry, RF field 218 penetrates generally from about 2" to about 4" into the log. Typical log diameters range from 3 inches to 7 inches. RF field 218 thus provides an adequate sampling of at least the upper portion of the log, which is where most of the moisture tends to accumulate. In certain instance, RF field 218 is used in some instances to sample almost the entire bulk of the log. The RF moisture-content measurements performed using the systems and methods described herein are therefore generally a bulk measurement of moisture content rather than just a surface measurement. A bulk type of measurement is generally preferred because the moisture content at or near surface 220S of ceramic material 220 is typically is different from the bulk moisture content.

Figure 5:
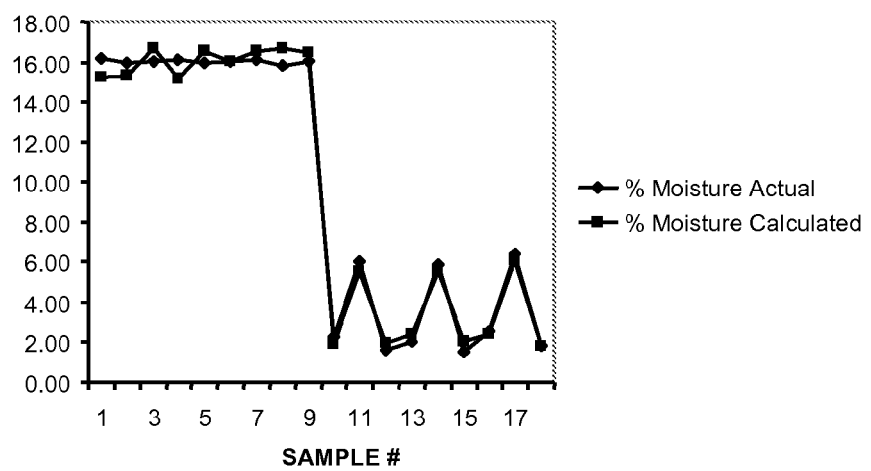
FIG. 5 is a calibration plot of the actual moisture content ("% moisture") of dried logs ("samples") measured using a destructive "loss on drying" method as compared to measurements made using an RF sensor system brought into contact with the dried logs.

FIG. 5 is a calibration plot of the actual moisture content ("% moisture") of dried logs ("samples") measured using a destructive "loss on drying" method as compared to measurements made using an RF sensor system 200 brought into contact with the dried logs. The calibration plot shows excellent agreement for the 17 sample logs.

In an example embodiment, RF sensor system 200 includes or is otherwise connected to a controller unit ("controller") 230. In one example, parallel-tuned circuit 212 is part of or is otherwise operably coupled to controller 230. Controller 230 includes a processor 232 configured to process a (raw or uncalibrated) moisture-content signal $S_M$ from the parallel-tuned circuit and generate a calibrated moisture-content measurement signal $S_C$. In an exemplary embodiment, processor 232 is or includes any processor or device capable of executing a series of software instructions and includes, without limitation, a general- or special-purpose microprocessor, finite state machine, controller, computer, central-processing unit (CPU), field-programmable gate array (FPGA), or digital signal processor.

Controller 230 also preferably includes a memory unit ("memory") 236 operably coupled to processor 232. As used herein, the term "memory" refers to any processor-readable medium or computer-readable medium, including but not limited to RAM, ROM, EPROM, PROM, EEPROM, disk, floppy disk, hard disk, CD-ROM, DVD, or the like, on which may be stored a series of instructions executable by processor 232. In an example embodiment, controller 230 includes a port or drive 240 adapted to accommodate a removable processor-readable medium 241, such as CD-ROM, DVE, memory stick or like storage medium.

The moisture-content measurement methods described herein may be implemented in various embodiments in a machine-readable medium (e.g., memory 236). In an exemplary embodiment, the machine-readable medium includes machine-readable instructions (e.g., computer programs and/or software modules) that cause processor 232 to perform calculations and/or operations for processing moisture-content signal $S_M$ to form calibrated moisture content measurement signal ("calibrated signal") $S_C$ using moisture-content calibration data stored in memory.

In an example embodiment, the computer programs run on processor 232 out of memory 236, and may be transferred thereto from permanent storage via disk drive or port 240 when stored on removable media 241, via a network connection or modem connection when stored outside of controller 230, or via other types of computer or machine-readable media from which it can be read and utilized.

Controller 230 optionally includes or is operably connected to a display 270 for displaying information using a wide variety of alphanumeric and graphical representations. For example, display 270 is useful for displaying moisture-content measurements based on calibrated signal $S_C$ in a form easily read by an operator of extrusion system 10. Controller 230 also optionally includes a data-entry device 272, such as a keyboard, that allows a system operator to manually input information into the controller, such as calibration information for a particular ceramic material 220. Example calibration information is described below.

Non-Contact Moisture Content Measurements

Certain ceramic materials lend themselves to a non-contact measurement, wherein RF antenna 208 is positioned at a standoff distance D from surface 220S of the ceramic material 220 being measured, such as shown in FIG. 4. Non-contact moisture-content measurements are particularly well-suited for ceramic materials having a relatively low dielectric constant.

Figure 6:
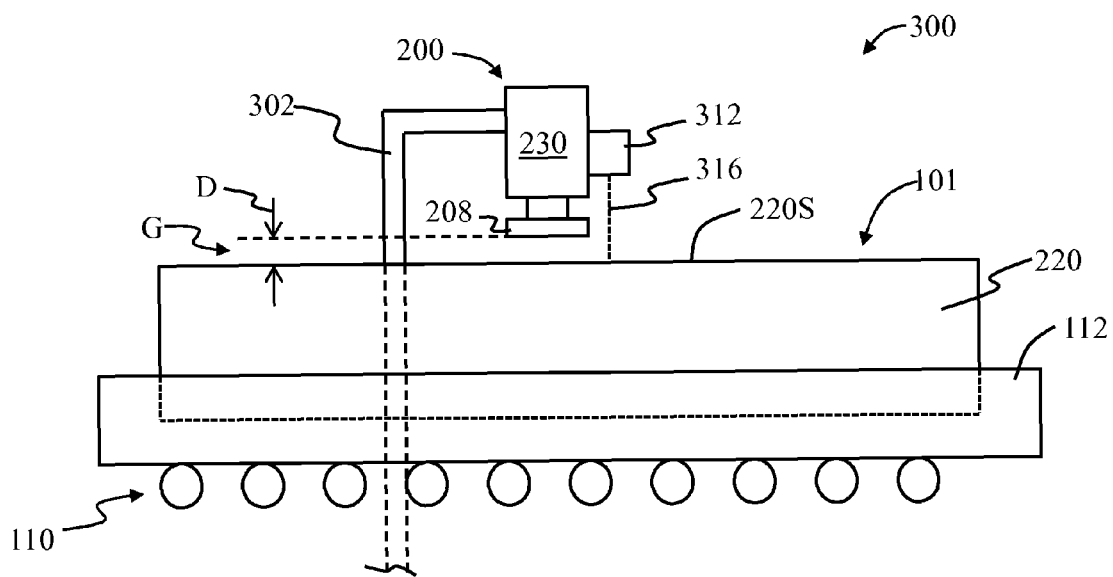
FIG. 6 is a schematic side view of a non-contact moisture-content measurement system as arranged relative to ceramic material in the form of a log supported by the conveyor in the extrusion system of FIG. 1.

FIG. 6 is a schematic side view of a non-contact moisture-content measurement system 300 as arranged relative to ceramic material 220 in the form of a log 101 carried in a carrier tray 112 and supported and conveyed by conveyor 110 in the extrusion system of FIG. 1. System 300 allows for an in-line, real-time measurement of the moisture content of ceramic material 220 in extrusion system 10, and in particular in logs 101.

RF sensor system 200 is supported by a support structure 302 relative to extrusion system 10 so that antenna 208 resides above ceramic material surface 220S at standoff distance D. This forms an air gap G between RF antenna 208 and ceramic material surface 220S. An exemplary antenna 208 for this measurement configuration is a planar-type antenna, such as an 8-inch open-frame planar antenna available for use with the aforementioned model RFM-1000 RF sensor system from Process Sensors Corporation. Antenna 208 typically has a central electrode (+ electrode) surrounded by an annular electrode (– electrode) (not shown). Antenna 208 is preferably positioned so that it is centered on the apex of log 101, i.e., so that the center electrode is aligned with the log apex.

The measurement of the dielectric constant of ceramic material 220 is impacted by the size (distance D) of gap G, as well as by the shape of the gap as defined by the shape (contour) of ceramic material surface 220S. Thus, in an exemplary embodiment of system 300, a distance measurement unit 312 is used to measure standoff distance D. In an example embodiment, distance measurement unit 312 includes a commercial laser sensor, such as model LKG87 available from Keyence Corporation, Osaka, Japan. Distance measurement unit 312 uses, for example, a laser beam 316 to establish a precise distance between ceramic material surface 220S and a reference point (not shown). Knowing the distance between antenna 208 and the reference point allows for standoff distance D to be precisely established.

In one example, standoff distance D=0.25 inches (6.35 mm) as measured relative to the apex of ceramic log 101. Variations in standoff distance D can be accounted for in the calibration so that this distance need not be maintained as fixed but can vary somewhat, as long as the standoff distance is known. In an alternative arrangement, sensors are used to maintain standoff distance D at a substantially fixed value.

Figure 7:
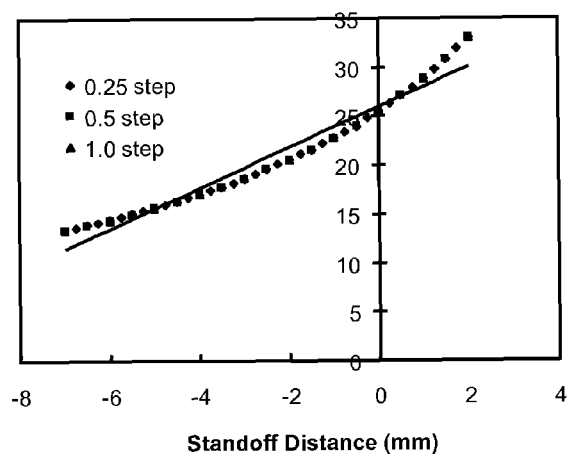
FIG. 7 is a plot of the RF sensor system output signal $S_M$ (arbitrary units) versus the standoff distance D (mm) for various standoff distance increments, illustrating the substantially linear relationship between these two parameters.

FIG. 7 is a plot of the RF sensor system output signal $S_M$ versus the standoff distance D (mm) for various standoff distance increments. The plot shows a very nearly linear relationship between the change in standoff distance D and the output signal $S_M$, thereby allowing for variations in the standoff distance D being incorporated into the moisture-content calibration.

In one approach, RF sensor system calibration is performed by creating logs 101 having different moisture contents and representative contours for surface 220S. Different log moistures are created, for example, by varying the amount of drying for the sample logs. The sample logs are first measured for moisture content by RF sensor system 200, and then are measured using another technique (e.g., the aforementioned off-line destructive "loss on drying" technique) to determine the actual moisture content.

Figure 8:
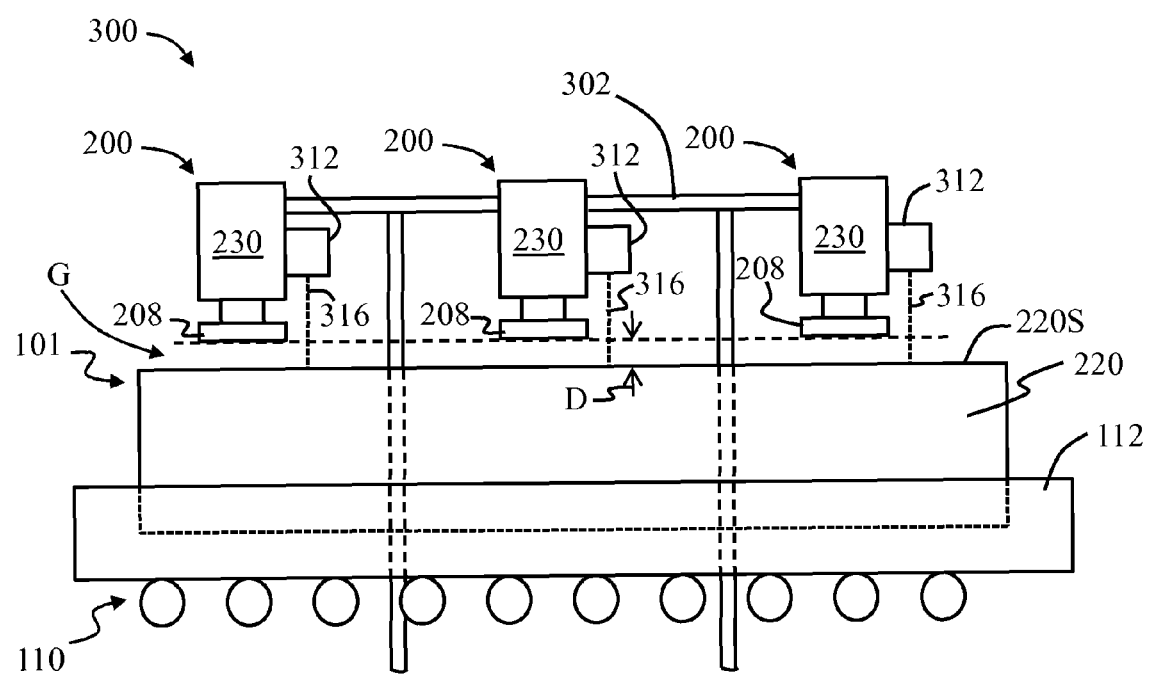
FIG. 8 is a schematic side view of an example non-contact moisture-content measurement system similar to that of FIG. 6, but that includes three RF sensor systems arranged along the length of the log.

Because dry logs 101 tend to have some variation in moisture content (i.e., the drying can be "spotty"), in an example embodiment multiple (e.g., three) RF sensor systems 200 are used to measure the moisture content at multiple positions along the log. FIG. 8 is a schematic side view of an example non-contact moisture-content measurement system 300 similar to that of FIG. 6, but that includes three RF sensor systems 200 arranged along the length of log 101. Generally, log 101 will generally not have a perfectly uniform cylindrical shape so that some variation in the respective standoff distances D typically occurs. Such variations, as mentioned above, are accounted for in the calibration process, and are measured using respective distance measurement units 312.

It should also be noted that the use of multiple RF sensor systems provides a faster measurement of the moisture content along the length of log 101 than can generally be accomplished by moving the log beneath a single RF sensor system to take multiple measurements. This is because the filter-forming process generally allows for the log to stop for only a brief amount of time (e.g., a few seconds) at the RF sensor system location before it needs to move on to the cutting station.

Contact Moisture-Content Measurements

Contact moisture-content measurements are preferred when ceramic material 220 has a relatively high dielectric constant, such as for the aforementioned AT-based ceramic materials. Contact measurements involve placing RF antenna 208 in contact with ceramic material 220. For contact measurements, RF antenna 208 preferably has a circular cross-section, such as a 3.5 inch diameter circular RF antenna available from Process Sensors Corporation.

Figure 9:
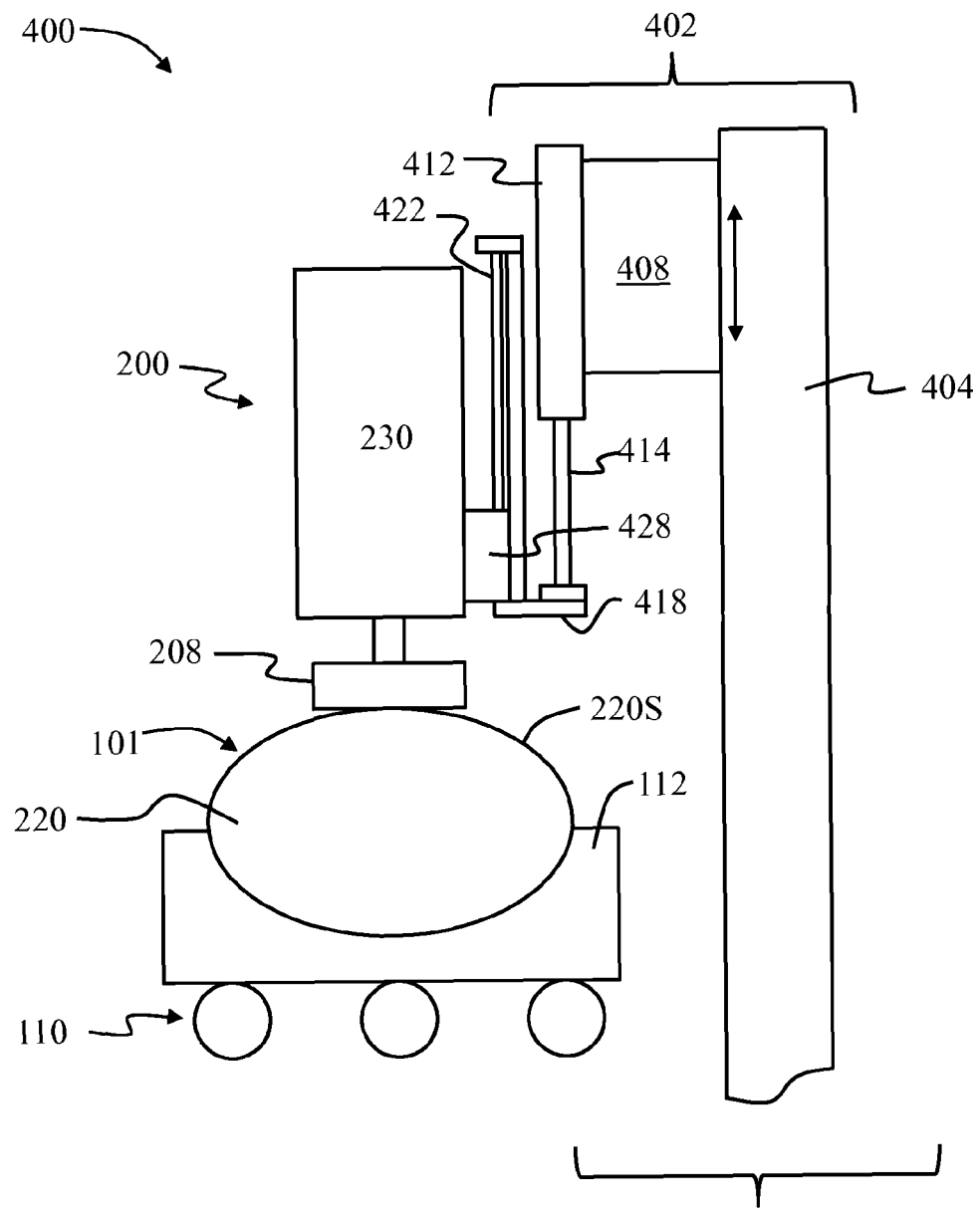
FIG. 9 is a schematic side view of a contact moisture-content measurement system as arranged relative to ceramic material in the form of a log supported by the conveyor in the extrusion system of FIG. 1.

FIG. 9 is a schematic diagram of a contact moisture-content measurement system 400 as arranged relative to ceramic material 220 in the form of a log 101 carried by carrier tray 112 and supported and conveyed by conveyor 110 in the extrusion system of FIG. 1. System 400 allows for a in-line, real-time measurement of the moisture content of ceramic material 220 in extrusion system 10, and in particular in logs 101.

System 400 includes a support structure 402 configured to movably support RF system 200 so that RF antenna 208 can contact surface 220S of ceramic material 220 making up log 101. Support structure 402 includes a main support member 404 and a servo-drive mounting unit 408 attached thereto and that can move up and down the support structure, as indicated by the double arrow, when servo motors (not shown) within the servo-drive mounting unit are activated. Servo-drive mounting unit 408 is attached to an air piston 412 that includes a piston rod 414. Piston rod 414 is attached at its end to an L-bracket assembly 418 that includes at least one rail 422.

RF sensor system 200 is slidably attached to at least one rail 422 via a rail mount 428. Support structure 402 thus forms a floating mount that allows for RF sensor system 200 to lightly contact ceramic material surface 220S by "floating" on at least one rail 422. Air piston 412 is configured to at least partially compensate for the weight of the RF sensor system 200 and its associated hardware. A counterweight system can also be used in place of the air piston. The floating mount configuration of support structure 402 allows RF antenna 208 to contact ceramic material 220 without damaging log 101.

Figure 10:
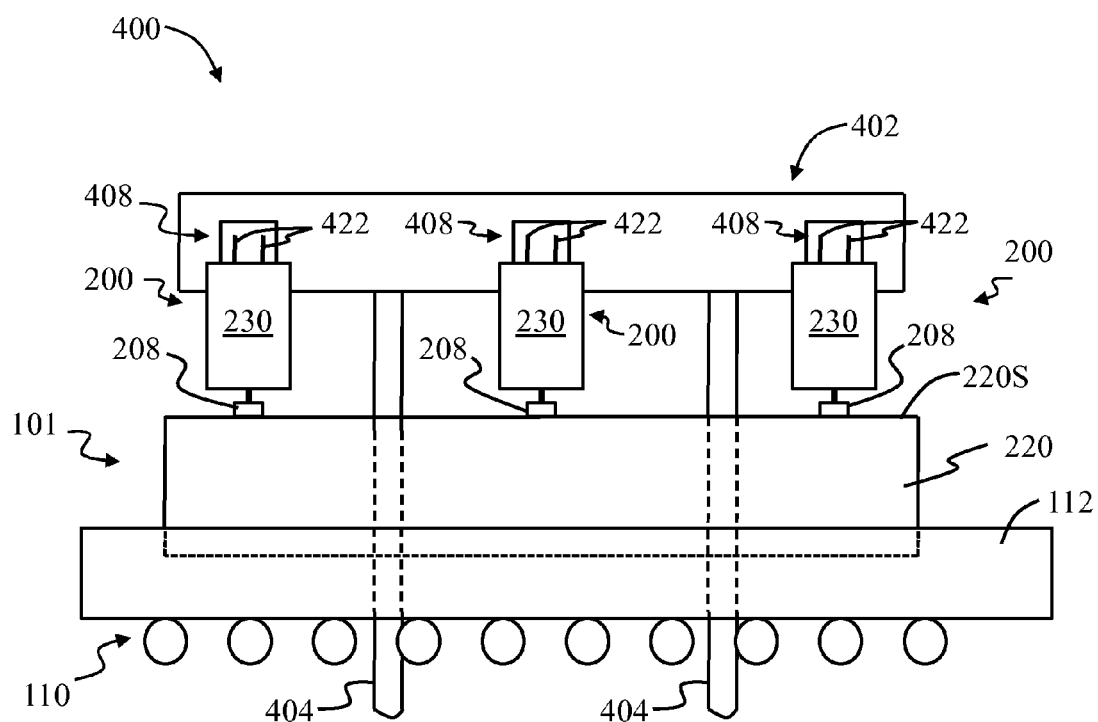
FIG. 10 is a schematic side view of an example contact moisture-content measurement system that includes three RF sensor systems similar to that shown in FIG. 9, arranged along the length of the log.

FIG. 10 is a schematic side view of an example moisture-content measurement system 400 similar to the non-contact system 300 of FIG. 8 and that includes three RF sensor systems 200 arranged along the length of log 101 and supported by support structure 402. In general, multiple RF sensor systems 200 can be used. As described above in connection with system 300 of FIG. 8 and the non-contact embodiment shown therein, using multiple RF sensor systems 200 in the contact embodiment allows for better sampling of log 101 to measure any variations in drying that occur along the length of the log.

Batch Material Moisture Measurement

With reference again to FIG. 1, an exemplary embodiment of the systems and methods described herein includes disposing antenna 208 through gap 72 in conveyor unit protective cover so RF field 218 is substantially entirely within a portion of batch material 34 traveling on conveyor 64. RF antenna 208 can either be in the non-contact or contact configuration. Because batch material 34 is typically only 1 to 2 inches thick, the output energy of RF sensor system 200 needs to be adjusted so that RF field 218 does not penetrate all the way through batch material 34 and reflect from underlying conveyor 64.

As batch material 34 makes its way from wet tower 20 down conveyer belt 64 and to extruder 90, its upper surface starts to dry out relative to the material below the surface. This means that a moisture measurement made on surface batch material will not accurately reflect the true moisture content of the bulk batch material being conveyed and extruded. Also, the water in the wet tower is weighed in water unit 50 before being added to the batch material in mixer 40. However, this process does not account for varying amounts of moisture in the incoming 'dry' batch material components due to environmental changes. It also does not account for variability in the process or the batch material 34 itself.

Accordingly, it is preferred to place RF antenna 208 in contact with batch material 34 so that it can remove or otherwise displace at least a portion of the top layer of batch material as the batch material is conveyed past the RF antenna. This results in a more accurate measure of the moisture content of batch material 34. It is also easier to use the contact configuration because there is no need to measure and maintain a certain standoff distance. In an exemplary embodiment, RF antenna 208 is arranged so that it penetrates the batch material surface, e.g., by a distance of about 1 mm to about 3 mm. This establishes better RF coupling to ceramic material 220 (i.e., the batch material 34) and thus provides a more consistent moisture-content measurement. This configuration also provides an in-line, real-time measurement of the moisture content of batch material 34.

Calibrating the Batch Material Moisture-Content Measurements

As discussed above, initial measurements taken by RF sensor system 200 are relative or "raw" measurements that need to be calibrated in order to provide an absolute or calibrated moisture content measurement. Accordingly, an aspect of the methods described herein includes establishing batch material calibration samples in connection with making batch material moisture-content measurements. The batch material calibration samples have the same material composition as the batch material to be extruded. These composition-specific calibration samples each have a select moisture content, typically provided by weighing exact amounts of water.

In an example embodiment, the water content of batch material 34 is measured as "% $H_2O$ minus percent dry weight without organics" or "% dry" for short. In this type of measurement, an amount of water (say X by weight) is added to an amount of dry batch material (say Y by weight) prior to any organics being added to the batch material. The water is then added to the dry batch material, giving a "% dry" of $\{[X/Y] \times 100\}\%$. The organics, if any are required, are then added to the batch material.

An RF sensor system measurement of each calibration sample is taken and the values ("calibration values") recorded and stored in controller 230, e.g., in memory unit 236. In an example embodiment, the calibration values are used to establish a look-up table, spreadsheet, or like arrangement of moisture content versus dielectric constant or voltage values for measurement signal $S_M$. Note that the sample measurements can be performed off-line.

In another example embodiment, the calibration values ("calibration data") are fitted to a calibration curve that is then used for translating raw moisture-content values (represented by signal $S_M$) to calibrated moisture-content values (represented by signal $S_C$) via processor 230. In an example embodiment, the calibrated moisture-content values and/or the calibration curve is/are displayed on display 270 for the benefit of the operators of extrusion system 10.

In one example, a regression fit is made of the raw moisture content measurement data to the actual amount of water (in % dry) added to the calibration samples. Once the data are fitted to an appropriate line, the slope and offset of this line are used (e.g., in processor 230 and memory 236) to calculate an offset for a particular batch material composition. The calibrated system data is then plotted against the actual data to show any potential error in the RF sensor system 200 after calibration.

At this point, batch material 34 can either continue to be extruded at extruder 90, with the extrudate now having a known and acceptable moisture content, or the extrusion process can be terminated if the moisture content is below a threshold value or moisture set point. In an example embodiment, the calibrated moisture content measurement is used to define a moisture set point for extrusion system 10. The moisture set point can be set, for example, in main controller MC, and serve to determine how much water is added to the batch material at wet tower 20 via water unit 50.

Adjusting the Moisture Content the Extrusion System

Once the moisture content of batch material 34 is known via a calibrated moisture-content measurement value, this value can serve as the basis for adjusting the batch material moisture content in extrusion system 10. In an example embodiment, the batch material moisture content is adjusted upstream of the position where the moisture-content measurement is made, e.g., in wet tower 20. The adjustment causes the moisture content to be closer to or equal to an idealized moisture content based on the calibrated moisture-content measurements.

In an example embodiment, the calibrated moisture-content value is provided to main controller MC, which adjusts the amount of water added to the batch material via water unit 50 in wet tower 20. In an example embodiment, the process of making a calibrated moisture-content measurement and adjusting the amount of water added to batch material 34 based on the calibrated measurement serves as a feedback system used to stabilize the extrusion process. In an example embodiment, this involves making repeated measurements of the batch material moisture content as the batch material 34 is conveyed to extruder 90 so as to provide frequent (e.g., minute-by-minute) calibrated moisture content measurements of the moving batch material.

Likewise, once a moisture-content measurement has been made for a log 101, a decision can then be made as to whether to proceed to cut the log into greenware pieces 102 for subsequent firing, or to discard the log because the moisture content does not meet the target moisture-content specification. Further, adjustments can be made to drying station 120 (either directly or via master controller MC) to ensure that subsequent logs are dried in a manner that meets the moisture-content specification. Such adjustments may include, for example, increasing the RF or MW energy in an RF or MW applicator in drying station 120, or increasing the amount of time logs 101 spend within the drying station.

It will be apparent to those skilled in the art that various modifications to the preferred embodiment of the invention as described herein can be made without departing from the spirit or scope of the invention as defined in the appended claims. Thus, it is intended that the present invention covers the modifications and variations of this invention provided they come within the scope of the appended claims and the equivalents thereto.

What is claimed is:

1. An in-line method of measuring a moisture content of ceramic material within an extrusion system used to form ceramic articles, comprising:
    arranging, relative to the extrusion system, at least one radio-frequency (RF) sensor system having an RF antenna, and generating through the RF antenna an RF field that resides substantially entirely within the ceramic material;
    in response to the RF field interacting with the ceramic material, generating in the RF sensor system a signal $S_M$ representative of a raw moisture-content measurement of the ceramic material;
    generating calibration data by performing RF moisture-content measurements on samples of the ceramic material having different known moisture contents; and
    establishing a calibrated moisture-content measurement using the raw moisture-content signal $S_M$ and the calibration data.

2. The measurement method according to claim 1, wherein the ceramic material has a surface, and further comprising:
    disposing the RF antenna at a standoff distance from the ceramic material surface and measuring the standoff distance; and
    wherein generating the calibration data includes performing non-contact RF moisture-content measurements on samples of the ceramic material at different standoff distances.

3. The measurement method according to claim 2, wherein the surface has a shape, and wherein generating the calibration data includes performing RF moisture-content measurements on samples of the ceramic material having said surface shape.

4. The measurement method according to claim 3, wherein the ceramic material is in the form of a substantially dried log.

5. The measurement method according to claim 4, including disposing multiple RF sensor systems along a length of the log, thereby establishing multiple calibrated moisture-content measurements at different log locations.

6. The measurement method according to claim 1, wherein the ceramic material is in the form of batch material not yet extruded.

7. The measurement method according to claim 1, wherein the ceramic material has a surface, and further comprising:

disposing the RF antenna so as to be in contact with the ceramic material surface; and wherein generating the calibration data includes performing RF contact moisture-content measurements on samples of the ceramic material having different moisture contents.

8. The measurement method according to claim 7, wherein the ceramic material is in the form of a substantially dried log.

9. The measurement method according to claim 7, including disposing multiple RF sensor systems along a length of the log, thereby establishing multiple calibrated moisture-content measurements at different log locations.

10. The measurement method according to claim 7, wherein the ceramic material is in the form of batch material that has not yet been extruded.

11. The measurement method according to claim 7, further comprising supporting the at least one RF sensor system on a floating mount configured to establish contact between the RF antenna and the ceramic material surface without damaging the ceramic material surface.

12. An in-line method of measuring a moisture content of a substantially dry log formed from ceramic material and having a surface with a shape, and used to form a ceramic article, comprising:

generating at least one radio-frequency (RF) field using at least one RF sensor arranged relative to the log so that the at least one RF field resides substantially entirely within the log;

in response to the at least one RF field interacting with the ceramic material in the log, measuring with the at least one RF sensor a corresponding at least one response signal representative of a raw moisture-content measurement in the log;

generating calibration data by performing RF moisture-content measurements on log samples made of the same ceramic material but having different known moisture contents; and using the calibration data and said at least one response signal to form at least one calibrated moisture-content measurement for the log.

13. The in-line moisture-content measurement method according to claim 12, further comprising:

disposing an RF antenna at a standoff distance from the log surface and measuring the standoff distance; and wherein said generating calibration data includes measuring samples having said log surface shape.

14. The in-line moisture-content measurement method according to claim 12, further comprising disposing an RF antenna in contact with the log surface.

15. The in-line moisture-content measurement method according to claim 12, further comprising:

arranging multiple RF sensors at different log locations;

measuring with the multiple RF sensors corresponding multiple responses representative of raw moisture-content measurements in the log at the different locations; and using the calibration data and said measured multiple responses to form calibrated moisture-content measurements for the log at the different locations.

16. An in-line system for measuring within an extrusion system a moisture content of ceramic material with a surface and used to form ceramic articles, comprising:

at least one radio-frequency (RF) sensor system having an RF antenna and arranged relative to the extrusion system, the least one RF sensor configured to generate an RF field through the RF antenna and substantially entirely within the ceramic material so as to generate a response signal $S_M$ that contains raw moisture-content information;

a computer-readable medium connected to or included within the at least one RF sensor and configured to store the raw moisture-content calibration information and to store calibration data obtained by performing RF moisture-content measurements on samples of the ceramic material having different known moisture contents; and a processor operably coupled to the computer readable medium and configured to execute instructions that cause the processor to calculate a calibrated moisture-content measurement based on the response signal $S_M$ and the calibration data stored in the computer-readable medium.

17. The measurement system according to claim 16, wherein:

the RF antenna is disposed at a standoff distance from the ceramic material surface;

the measurement system further includes a distance measurement unit configured to measure the standoff distance; and wherein the calibration data stored in the computer-readable medium includes non-contact RF moisture-content measurements on samples of the ceramic material at different standoff distances.

18. The measurement system according to claim 17, wherein the surface has a shape, and wherein the calibration data stored in the computer-readable medium includes RF moisture-content measurements on samples of the ceramic material having said surface shape.

19. The measurement system according to claim 16, wherein the RF antenna is disposed so as to be in contact with the ceramic material surface, and wherein the calibration data stored in the computer-readable medium includes RF contact moisture-content measurements on samples of the ceramic material having different moisture contents.

20. The measurement system according to claim 19, wherein the at least one RF sensor system is supported by a floating mount configured to establish contact between the RF antenna and the ceramic material surface without damaging the ceramic material surface.

* * * * *